(12) United States Patent
Kutushov

(10) Patent No.: US 7,888,284 B2
(45) Date of Patent: Feb. 15, 2011

(54) MAGNETICALLY OPERATED ABSORBENT AND METHOD FOR THE PRODUCTION THEREOF

(75) Inventor: Mikhail Vladimirovich Kutushov, Moscow (RU)

(73) Assignees: Evgeny Pavlovich Germanov, Moscow (RU); Mikhail Vladimirovich Kutushov, Moscow (RU)

( * ) Notice: Subject to any disclaimer, the term of this patent is extended or adjusted under 35 U.S.C. 154(b) by 0 days.

(21) Appl. No.: 12/496,396

(22) Filed: Jul. 1, 2009

(65) Prior Publication Data

US 2009/0305868 A1 Dec. 10, 2009

Related U.S. Application Data

(62) Division of application No. 10/575,830, filed on Apr. 14, 2006, now abandoned.

(51) Int. Cl.
*B01J 20/00* (2006.01)

(52) U.S. Cl. .................. 502/400; 75/10.19; 75/10.2; 75/10.22; 75/10.29; 75/10.67; 419/1; 419/23; 502/5; 502/406

(58) Field of Classification Search .............. 75/1, 75/23; 419/10.19, 10.2, 10.22, 10.29, 10.67; 502/5, 400, 406

See application file for complete search history.

(56) References Cited

U.S. PATENT DOCUMENTS 3,419,901 A * 12/1968 Nordhlom .................. 205/74
5,980,479 A    11/1999 Kutushov
6,136,428 A    10/2000 Truong et al.
6,544,352 B2 *  4/2003 Mitani et al. ............... 148/104
6,616,623 B1    9/2003 Kutushov
2007/0071977 A1  3/2007 Kutushov

FOREIGN PATENT DOCUMENTS

| JP | 04013801 A * | 1/1992 |
| RU | 2065606 | 8/1996 |
| RU | 2109522 | 4/1998 |
| RU | 2178313 | 1/2002 |
| SU | 1589327 | 8/1990 |

OTHER PUBLICATIONS

English translation of RU2178313 to Kutushov. Translated by the McElroy Translation Company on Nov. 2009.*

* cited by examiner

*Primary Examiner*—Scott Kastler
*Assistant Examiner*—Brian Walck
(74) *Attorney, Agent, or Firm*—Pauley Petersen & Erickson

(57) ABSTRACT

An absorbent includes a ferromagnetic nucleus with a one-layer or two-layer shell or devoid thereof and the nucleus is embodied in the form of a plate with a planar size that ranges from 500-5000 μm and the thickness is equal to 0.1-1000 μm. The method for producing the inventive magnetically-operated absorbent includes evaporating and/or melting a magnetic material powder in a low-temperature plasma, quenching and condensing the thus obtained vaporized and/or melt-particle product in a gas flux, and transferring the product precipitated in the form of crystals or micro slugs of corresponding metals, correspondingly to a stabilizer-containing dispersion medium and holding in the medium until a gas release is over. Then the crystals or micro slugs are processed by flattening, for example pressing so that the plates of a specified thickness are obtained.

15 Claims, No Drawings

MAGNETICALLY OPERATED ABSORBENT AND METHOD FOR THE PRODUCTION THEREOF

CROSS REFERENCE TO RELATED APPLICATION

This application is a divisional of U.S. application Ser. No. 10/575,830, filed on 14 Apr. 2006 now abandoned. The parent application is hereby incorporated by reference herein in its entirety and is made a part hereof, including but not limited to those portions which specifically appear hereinafter.

BACKGROUND OF THE INVENTION

1. Field of the Invention

This invention relates to biology and medicine and might be applied for biological fluids purification and to normalize a condition of those to physiological standards.

2. Discussion of Related Art

There is a known ferreed sorbent (FS), made of iron in the form of crystals with particle size of 10-15 nm, as taught by USSR Patent Reference 1589327, dated Apr. 14, 1988.

While exerting bactericidal effects, the known sorbent is limited in applicability because it can be used "in vitro" only.

The closest analogical prototype product is ferreed sorbent (FS), with the atomic centre or core as grading fraction with particle size of (0.1-1000) mc, made of iron, iron oxides, nickel, or iron-nickel alloy, and coated with a single or double layer coat of carbon, aluminum oxide, silicium dioxide, zirconium dioxide, dextran, e.g. SEPHADEX®, gelatin, albumin, polysaccharide, e.g. amylum, or ion-exchange resins, e.g. cations or anions, where the coat upper layer is either conjugated with antibodies, or modified by pharmaceutical composition, e.g. antibiotics or phthalhydrazide salines, e.g. 5-amino-2,3-dihydro-1,4-dione salines, or else fermented e.g. with urease, such as taught by Russian Federation Patent 2178313, dated Aug. 29, 2000.

The above sorbent appears to be an effective remedy used for biological fluids extracorporal restoration to physiological standards, providing clearance of e.g. blood from low-molecular, medium-molecular and high-molecular exotoxines and endotoxines with distraction of its rheological properties, correction of biological fluids enzymatic and immune constitution, as well as antisepsis of viruses and retroviruses pathogenic microflora. However, as such sorbent turns up a very expensive product, and a great quantity of the above sorbent is needed for an appropriate course of treatment, and consequently the treatment is related with significant financial expenses.

There is a known method of ferreed sorbent preparation technique taught by USSR Patent Reference 1589327, dated Apr. 14, 1988, including an iron powder volatilization procedure at low temperature ($10^4 \times (0.5\text{-}5)°$ K) plasma in an argon atmosphere, and the derived volatile product is quenched and condensed in an argon gas flow. Then, the precipitated product in the form of crystals is transferred to a stabilizer containing dispersion medium, e.g. water at pH 7-9 or oil, and sustained there while being mixed, within (10-15) hours at the temperature $(50\text{-}90)°$ C. and at residual pressure of (1-3) mmHg until the end of gas liberation.

The known method provides the possibility to derivate sorbent in the form of iron particles (crystals) with particle size of (10-15) nm, however, due to small particle size the above sorbent has got low magnetic susceptibility values, consequently in order to withdraw sorbent out of the biological medium application of magnetic fields with intensity (1-3) tesla is required, which is unacceptable by medical norms, such as taught by Russian Federation Patent 2109522, dated Aug. 1, 1996.

One analogical prototype of ferreed sorbent preparation technique is taught by Russian Federation Patent 2109522, dated Aug. 1, 1996, and includes fractionating of high dispersed powder of Ferram reductum in inert gas flow with the velocity of (0.02-1.00) m/s under exposure of a magnetic field with an intensity of $(10\text{-}10^3)$ A/u with subsequent thermal treatment of received iron particles at the temperature of $(1000\text{-}1500)°$ C. in inert gas flow containing coal and/or silicon oxide and/or aluminium oxide microparticles, after which treatment the ferreed sorbent particles surface are covered by biologically active compounds, such as food proteins or dextran, or pharmaceutical preparations, or antibodies.

Such method provides a possibility to receive ferreed sorbent of certain chemical composition, effective at recession in vivo and in vitro of low, medium and high molecular toxins, microflora and retroviruses. However, the above method is limited to receiving the ferreed sorbent with volumetrical particles, having predominantly proportionate dimensions with respect to both thickness of (0.5-2.5) μm and those particles surface dimensions corresponding to that form.

SUMMARY OF THE INVENTION

One object of the "Ferreed Sorbent" invention is to develop the sorbent similar in performance to analogous sorbent having substantially larger particles surface without any significant increase in weight of the sorbent core.

Another object of the "Ferreed Sorbent" invention is to develop the procedure of receiving the sorbent with the core in a form of e.g. flake.

The above and other objects are achieved with the ferreed sorbent having a ferromagnetic core, with a single or double layer coat or no coat, and the core made in a form of a flake, with in-plane dimensions of (500-5000) μm, and thickness of (0.1-1000) μm. Here the core is made either of iron, nickel, iron-nickel alloy, iron or nickel alloy with titanium, iron or nickel alloy with tantalum, iron-nickel-titanium alloy, or iron-nickel-tantalum alloy.

Furthermore, the one layer coat is made either of carbon, aluminum oxides, silicon dioxide, zirconium dioxide, dextran, e.g. from SEPHADEX®, gelatin or albumin, polysaccharide, e.g. amylum, or ion-exchange resins, e.g. cations or anions.

Here, in double layer coat the first closest to the core or inner layer is made either of carbon, aluminum oxides, silicon dioxide, zirconium dioxide, and the second or outer layer of the coat is made either of dextran, e.g. from SEPHADEX®, or gelatin or albumin, polysaccharide, e.g. amylum, or ion-exchange resins, e.g. cations or anions.

Also, the outer layer of the coat is either conjugated with antibodies, or modified by pharmaceutical composition, e.g. antibiotics or phthalhydrazide salines, e.g. 5-amino-2,3-dihydro-1,4-dione salines, or else fermented e.g. with urease.

The above and other objects are achieved by the fact that in the ferreed sorbent generation method, iron, nickel, titanium and/or tantalum powder is volatilized or fused in a low-temperature plasma with the temperature of $10^4 \times (0.5\text{-}5)$K, and a received product of vaporous or fused particles of respective metals or respective metals alloys is quenched and condensed in a gas flow, e.g. an argon flow, and then the product settled as crystals or, correspondingly, as microbars of respective metals alloys, is transferred to a disperse medium containing stabilizer, e.g. water and/or oil, and while being mixed, sustained there within (5-15) hours at the temperature $(50\text{-}90)°$ C. and at residual pressure of (1-5) mmHg until gas liberation ends. Then, those crystals or microbars are treated by flattening e.g. through pressing e.g. in a ball mill, until flakes are of the specified thickness, and afterwards are repeatedly (up to 10 times) washed in distilled water, and then separated from weak parts of flakes, treating with e.g. ultrasound of e.g. (200-300) W/cm$^2$ capacity. Then, the received flakes are dried out e.g. in a hot air sterilizer at the temperature of (80-110)° C., and after that the dried flakes are fractionated in either an inert gas flow with the velocity of (0.02-1.00) m/s under exposure of magnetic field of 5×(10-10$^3$) A/m intensity, or by using e.g. centrifugation. Then, the specified size sorbent cores with a layer-by-layer formed coat are extracted, and the received end product is packed in light-protected and hermetically sealed containers and sterilized, by e.g. U-rays, where sorbent received right after fractionating can be used as the end product.

Here, the first or inner layer of the coat is formed by thermal treatment of fractionated flakes at the temperature of (1000-1500)° C. in an inert gas flow, e.g. a flow of argon, containing microparticles of either carbon, silicon dioxide oxide, aluminum oxide, or zirconium oxide.

Furthermore, the first layer of the coat is formed by blending with and using ultrasound exposure to fractionated flakes suspension within (1-10) minutes in heated to the temperature of (30-80)° C. aqueous solution of dextran, gelatin or albumin, or amylum, with subsequent cooling of the above suspension down to the temperature of (4-10)° C., and the received precipitate is filled up with formalin, sustained there within (10-40) minutes, simultaneously being mixed, and after that dried out thoroughly at the temperature of (25-50)° C. and grinded, then the received sorbent capsules, the end product, are filtered in a magnetic field.

Furthermore, the first layer of the coat is formed through adding an ion-exchange resin, e.g. amberlite into a fractionated flakes suspension in distilled water, heated up to the temperature of (40-60)° C., with subsequent cooling of the above suspension down to the temperature of (15-30)° C., with adding nitrous acid ($HNO_2$) diluted in water, sustaining within (10-15) minutes, cooling down to the temperature of (4-10)° C. and elution of precipitate which is washed in a physiological solution and buffered in an aqueous solution of $NH_4OH$ foundation blend and $NH_4Cl$ salt.

Here, the second layer of the coat is formed by blending with using ultrasound exposure within (1-10) minutes to a suspension of ferromagnetics covered with carbon or silicon dioxide, aluminium oxide, zirconium oxide coat in aqueous solution of dextran, gelatin, albumin, or amylum heated up to the temperature (30-80)° C. with subsequent cooling of the above suspension down to the temperature (4-10)° C. The received precipitate is filled up with formalin, sustained in there within (10-40) minutes of simultaneously being mixed, then dried out thoroughly at the temperature of (25-50)° C., grinded and the received sorbent capsules, of the end product, are filtered in a magnetic field.

Furthermore, the second layer of the coat is formed through adding an ion-exchange resin, e.g. amberlite into a heated, up to the temperature of (40-60)° C., suspension of ferromagnetics, covered with carbon or silicon oxide, aluminium oxide, or zirconium oxide coat, in distilled water, with subsequent cooling of the above suspension down to the temperature of (15-30)° C., and adding and immixturing albumin, e.g. in the form of serum, with subsequent adding of nitrous acid ($HNO_2$) diluted in water, sustaining within (10-15) minutes, cooling down to the temperature of (4-10)° C. and elution of precipitate which is activated by sustaining within (1.5-2) hours in a modifier solution, then washed in physiological solution and buffered in aqueous solution of $NH_4OH$ foundation blend and $NH_4Cl$ salt.

Sodium periodate ($NaIO_4$) or glutaric dialdehyde in (3-10) % solution of $Na_2SO_4$ in water can be used here as a modifier.

Furthermore, while forming the outer layer of the coat, it is conjugated with antibodies by adding the ferreed sorbent with a single or double layer coat into aqueous suspension; but it should be with the outer coat layer made of SEPHADEX® or albumin, modified e.g. with glutaric dialdehyde or sodium periodate, with serum, e.g. of blood, containing antibodies, specified to sorbed antigen, e.g. to systemic lupus erythematosus antigen, in buffered liquid with pH of 6.5-10, sustaining while being mixed of the above compound within (1-3) hours at the temperature of (15-25)° C., subsequent to adding to the compound of sodium borhydrate, cooling down to the temperature of (4-10)° C., and repeated sustaining while being mixed within (1-3) hours, precipitate extraction and its buffering and drying out.

Furthermore, while forming the outer layer of the coat, it is modified with pharmaceutical composition through heating the ferreed sorbent suspension with a single or double layer coat, but with the outer coat made of e.g. dextrane or gelatin, up to the temperature of (35-70)° C. in physiological solution, and adding into it a pharmaceutical composition in powder, e.g. antibiotic, e.g. oxaccillin, sustaining at thorough mixing at the above mentioned temperature within (0.5-2.5) hours, a subsequent cooling of the compound down to the temperature of (4-10)° C., decanting of a supernatant fluid in a magnetic field, and washing the precipitate in running distilled water and its subsequent drying out.

Furthermore, while forming the outer layer of the coat, it is modified through preliminary dissolution of urease crystals in polyether, e.g. dibenzo-18 crown 6, immixture of the above solution with the suspension in distilled water of ferreed sorbent with the coat made of e.g. SEPHADEX®, sustaining while being mixed at the temperature of (25-40)° C. within (2-5) hours and cooling down to the temperature of (4-10)° C., subsequently adding of formaldehyde and repeated sustaining within (1-3) hours, and draining out the supernatant fluid in the presence of a magnetic field and drying out the precipitate.

Furthermore, while forming the outer layer of the coat, it is modified through a heating up of an aqueous suspension of the ferreed sorbent with the coat made of e.g. dextran, to the temperature of (40-70)° C., a subsequent immixture with zirconium saline powder, e.g. of respective phthalhydrazide saline, and (50-120) W/см$^2$ intensity ultrasound exposure to the above mixture within (1-10) minutes, a cooling of the received compound down to the temperature of (4-10)° C., adding formaldehyde, sustaining while being mixed within (1-3) hours, and draining out the supernatant fluid in the presence of a magnetic field and drying out the precipitate.

DETAILED DESCRIPTION OF THE INVENTION

Ferreed sorbent is made in the form of cores with a single or double layer coat surrounding the core, and with no coating.

To be used as cores for the ferreed sorbent powder is taken from ferromagnets, e.g. from iron (Fe), its oxides ($Fe_2O_3$ or $Fe_3O_4$) nickel (Ni), iron-nickel alloys, as well as from iron or nickel alloy with titanium (Ti), from iron or nickel alloy with tantalum (Ta), from iron-nickel-titanium alloy, or from iron-nickel-tantalum-titanium alloy and the like magnetic sensible materials.

For the subsequent use fractions in the form of flakes with the dimensions in plane of (500-5000) μm and with the thickness of (0.1-1000) μm are taken.

For getting cores for the ferreed sorbent, iron, nickel, titanium, and/or tantalum powder with particle size of $(10^2-10^5)$ nm is volatilized and/or fused in low-temperature plasma with the temperature of $10^4 \times (0.5-5)$K, and the received product volatized and/or fused in the form of respective metals or respective metals alloys with concentration of (0.1-0.5) volume % quenched down to the temperature of (50-80)° C. and condensed in a reactor, such as taught by USSR Patent Reference 1589327, in a gas flow, e.g. in an argon flow, and then the product settled in the form of crystals or, respectively, microbars of respective metals alloys, e.g. in the amount of (0.05-10) mg, is transferred to the disperse medium containing stabilizer, e.g. distilled water of (50-500) ml with pH of 7-9 and/or mineral, e.g. paraffin or vegetable oil e.g. olive or sea-buckthorn oil, with preliminarily added e.g. oleic acid in the amount of (2-20) volume %, and, while being mixed, sustained in there within (5-15) hours at the temperature of (50-90)° C. and at the residual pressure of (1-5) mmHg until the end of gas liberation.

After that those crystals or microbars are treated by flattering, e.g. through pressing e.g. in a ball mill, until having flakes of the specified thickness, which then repeatedly (up to 10 times) are washed in distilled water, and then weak flake parts are removed by exposing to ultrasound of e.g. (200-300) W/cm² intensity in e.g. water.

The received material, different size flakes and chip bits, is dried in whole e.g. in a hot air sterilizer at the temperature of (80-110)° C., and then the dried product or flakes is fractionated either in inert gas flow with velocity of (0.02-1.00) m/s under the exposure of magnetic field with intensity of $5 \times (10-10^3)$ A/м or by using centrifugation. The sorbent or flakes of the specified size is excreted in the form of cores, on which coats are formed layer by layer, and the acquired end product is packed up in lightproof hermetically closed containers and sterilized through e.g. U-rays. Here, the sorbent received right after fractionating can be chosen as the end product as well. The output of conditioned sorbent cores after fractionating makes (60-75) %.

For getting or forming of the first, closest to the core, layer of the coat, the fractionated flakes are treated at the temperature of (1000-1500)° C. in a thermo oven in inert gas flow, e.g. in argon flow, containing microparticles of carbon (C), silicon dioxide ($SiO_2$), aluminum oxide ($Al_2O_3$ or $Al_3O_4$), or zirconium oxide ($ZrO_2$). A flow velocity makes (0.02-1.2) m/s. Coating quality of cores depends on inert gas flow throughput rate, as well as on saturation of the gas with microparticles of coating material and the size of those particles. In the given examples, the thickness of the coat layer made with the above method makes (0.2-50) μm.

The efficient output of the sorbent is (70-85) %.

While forming the first layer of the coat through covering sorbent cores with such substances like either dextran, gelatin, albumin, or amylum, a fractionated flakes suspension in the amount of (2-20) g in (10-50) ml of distilled water is mixed with (50-100) ml of a heated to the temperature of (30-80)° C. aqueous solution of either dextran, gelatin, albumin, or amylum, with the blend ratio of (volume %):(50-95) % of the respective product, the rest is water; then is mixed within (1-10) minutes until it gets homogeneous structure under the exposure of e.g. ultrasound disperser "UZDN-2T", such as taught by USSR Patent Reference 1684616, and ultrasound with an oscillation frequency (10-15) kHz and an intensity rate of (50-120) Wt/cm. Then the suspension is cooled e.g. in a refrigerator down to the temperature of (4-10)° C., then the precipitate received is filled up with formalin (aqueous solution HCHO), sustained in there within (10-40) minutes while simultaneously being mixed, and after that can be thoroughly dried up at the temperature of (25-50)° C., grinded and the received sorbent capsules, the end product, are filtered in magnetic field with the intensity of $5 \times (10-10^3)$ A/m, of e.g. constant magnet made of samarium (8t)-cobalt (Co) alloy.

A thickness of the coat layer made using the method above makes (0.5-3) mm.

The quantitative output of sorbent makes (85-95) % out of the initial.

While forming the first layer of the coat by using ion-exchange resin, e.g. (10-25) g of amberlite is added into the heated up to the temperature of (40-60)° C. fractionated flakes suspension of (2-5) g per (10-100) ml of distilled water, then the received compound is cooled down to the temperature of (15-30)° C., then added is nitrous acid ($HNO_3$) diluted in water (in the amount of (1-10) vol. %), sustained within (10-15) minutes, then cooled again down to the temperature of (4-10)° C. and then precipitate is excreted, which is washed in a physiological solution, and buffered until it gets pH 4.0±0.5 in the aqueous solution of foundation of $NH_4OH$ or $NH_4Cl$ saline.

A thickness of the coat layer made by the above method makes (0.2-1) mm.

The quantitative output of sorbent makes (90-92) % out of the initial.

While forming the second layer of the coat through covering the ferreed sorbent coated with either carbon or silicon oxide or aluminum oxide, or zirconium oxide with such substances like either dextran, gelatin, albumin, or amylum, a suspension of ferromagnetics, in the amount of (2-20) g per (10-50) ml of distilled water, covered with a carbon, silicon oxide, aluminum oxide, or zirconium oxide coat, being mixed within (1-10) minutes under the exposure of ultrasound with intensity of (50-120) W/cm² in (50-100) ml of heated to the temperature of (30-80)° C. (50-95) % solution of dextran, gelatin, albumin, or amylum in distilled water with a subsequent cooling to the above suspension down to the temperature (4-10)° C. The precipitate is filled up with formalin, sustained in there within (10-40) minutes while simultaneously being mixed and after that it is thoroughly dried out at the temperature of (25-50)° C., grinded, and the acquired sorbent capsules or end product are filtered in magnetic field with the intensity of $5 \times (10-10^3)$ A/m.

The thickness of the coat layer made by the above method makes (0.5-3) mm.

The quantitative output of sorbent makes (85-95) % out of the initial.

While forming the second layer of the coat by using ion-exchange resin, a suspension of ferromagnetics, in the amount of (0.2-0.5) g per (10-100) ml of distilled water, covered with a carbon, silicon oxide, aluminum oxide, or zirconium oxide coat, is heated up to the temperature of (40-60)° C., then e.g (1-2) g of amberlite is added into there, and then the received compound is cooled down to the temperature of (15-30)° C. Then nitrous acid ($HNO_3$) diluted in water, in the amount of (1-10) vol. %, is added, sustained within (10-15) minutes, then cooled again down to the temperature (4-10)° C. and the precipitate is excreted, which is activated by sustaining within (1.5-2) hours in a modifier solution, then washed in a physiological solution and buffered until it gets to pH 4.0±0.5 in aqueous solution of $NH_4OH$ foundation and $NH_4Cl$ salt. Here, sodium periodate ($NaIO_4$) or glutaric dialdehyde in a (3-10) % solution of $Na_2SO_4$ in water can be used as a modifier.

The thickness of the coat layer made by the above method makes (0.2-1) mm.

The quantitative output of sorbent makes (90-95) % out of the initial.

Moreover, while forming the outer layer of the coat, it is conjugated with antibodies through adding serum e.g. of blood, into an aqueous suspension of ferreed sorbent with a single or double coated, but with the outer coat made from sephadex or albumin, modified with e.g. glutaric dialdehyde or sodium periodate, in the amount of (1-50) ml of serum per (100-150) ml of suspension, containing antibodies specific to the antigen sorbed, e.g. to systemic lupus erythematosus antigen, in buffering liquid with pH of 6.5-10, sustaining while the compound being mixed within (1-3) hours at the temperature of (15-25)° C., with subsequent adding of sodium borhydrate into the compound, cooling down to the temperature of (4-10)° C., repeated sustaining with simultaneous mixing within (1-3) hours, and the precipitate extraction and its buffering and drying out.

Here the respective coat layer thickness is increased for (0.2-0.5) mm.

The quantitative output of sorbent makes (92-95) % out of the initial.

Furthermore, while forming the outer layer of the coat, it is modified with a pharmaceutical composition by heating up to the temperature of (35-70)° C. of aqueous suspension of ferreed sorbent, (10-20) g of sorbent per (50) ml of distilled water, with a single or double layer coat, but the outer coat made of e.g. dextran, or gelatin, in physiological solution (0.9% solution of NaCl in distilled water), and adding a pharmaceutical preparation powder, in the amount of (1-5) r per (10-50) ml of suspension, e.g. antibiotic, e.g. oxaccillin, sustaining while simultaneous thorough mixing at the above mentioned temperature within (0.5-2.5) hours, subsequent cooling of the above compound down to the temperature of (4-10)° C., decanting of the supernatant fluid in magnetic field with the intensity of $5\times(10\text{-}10^3)$ A/m, washing the precipitate in running distilled water and its subsequent drying out at the temperature of (25-40)° C.

Here the respective coat layer thickness is increased for (0.01-0.1) mm.

The quantitative output of sorbent makes (90-95) % out of the initial.

Furthermore, while forming of the outer layer of the coat, it is modified by preliminary dilution of e.g. (1-5) g of urease crystals in (10-15) ml of polyether, e.g. of dibenzo-18 crown 6, blending the above solution with ferreed sorbent suspension in distilled water ((10-15) hg of sorbent per (50-100) ml of water) with the coat made e.g. from sephadex-10, sustaining while mixed at the temperature of (25-40)° C. within (2-5) hours and cooling down to the temperature of (4-10)° C., and subsequent adding of formaldehyde ((25-30) ml per 100 ml of compound) and repeated sustaining while mixed within (1-3) hours, pouring out the supernatant fluid under the influence of magnetic field with the intensity of $5\times(10\text{-}10^3)$ A/m and precipitate drying out e.g. in a hot air sterilizer at the temperature of (50-85)° C.

Here the respective coat layer thickness is increased for (0.5-1) mm.

The quantitative output of sorbent makes (90-95) % out of the initial.

Furthermore, while forming the outer layer of the coat, it is modified through heating of aqueous suspension of ferreed sorbent with e.g. dextran coat up ((15-20) g of sorbent per 75-100 ml of distilled water) to the temperature of (40-70)° C., and subsequent blending with zirconium saline powder of e.g. respective phthalhydrazide saline, e.g. 5-amino-2,3-dihydro-1,4-dion, and treating the above compound within (1-10) minutes with ultrasound of (15-25) kHz oscillation frequency and (50-120) W/cm$^2$ intensity, cooling of the received compound down to the temperature (4-10)° C., adding formaldehyde ((25-30) ml per 100 ml of compound), sustaining in there while mixing within (1-3) hours, and pouring out of supernatant fluid in the presence of magnetic field with the intensity of $5\times(10\text{-}10^3)$ A/m and precipitate drying out at the temperature of (25-45) C.

Here the respective coat layer thickness is increased for (0.01-0.1) mm.

The quantitative output of sorbent makes (90-95) % out of the initial.

INDUSTRIAL APPLICABILITY

Use of a ferreed sorbent having a substantially larger surface of the particles with no significant weight increase of its core, and the method of receiving such sorbent provides effective cleaning of biological fluids, e.g. blood, out of low-, medium- and high-molecular exotoxines and endotoxines without disorder of its rheological properties, provide possibility to correct ferment and immune structure of the biological fluids, as well as destruction of viruses and retroviruses pathogenic microflora while using appreciably low amount of the proposed ferreed sorbent, with respect to weight, relatively to the amount of the analogous sorbent known earlier and specified for the same purposes.

Thus, in view of the fact that biological fluid cleaning by using ferreed sorbent takes place by interaction of its surface with the fluid being corrected, one can show that the effective particle surface of the known sorbent, a size of which in terms of length, width and thickness are on average commensurable at mass conservation, is significantly smaller than the surface of the proposed sorbent.

For example, consider a spherical particle.

Using known mathematical formulas, we get the following as sphere volume value ($V_{sphere}$) which is equal to:

$V_{sphere}=4\pi r^3/3$, where r is sphere radius, and accordingly, the sphere surface area ($S_{sphere}$) is equal to $S_{sphere}=4\pi r^2$, then $S_{sphere}=3V_{sphere}/r$ Considering that the particle mass is proportional to its volume, and assuming that after the above described procedure of acquiring sorbent particles in the form of flakes, a spherical sorbent particle will be reformed into a round flake/disk. Then as the flake volume is $V_{flake}=\pi R^2\delta$, and the surface area $S_{flake}=\pi R^2$, where R—flake radius, and δ—its thickness, while δ=0.1 g (in accordance with the above said statement about some decrease of particle thickness), then $S_{flake}=V_{flake}/0.1$ g.

Considering that $V_{flake}=V_{sphere}$, then, as their masses are equal, we get the following:

$$S_{flake}=10V_{sphere}/r$$

Taking into consideration that, there are two such surfaces on the flake, and putting the term (1) into the formula (2) we get the following:

$$S_{flake's\,full\,surface}=20S_{sphere}/3$$

The results received justify the above hypothesis that in the case of using the sorbent being proposed, each particle surface interacting with a biological fluid is significantly enlarged, and, consequently, consumption of sorbent and respective treatment costs are decreased.

Feasibility of effective application of the proposed ferreed sorbent extracted using the above-described methods are confirmed by the following examples:

Example 1

A non-pedigree dog weighing 12 kilos was injected (per os) 4.3 g of veronal. After 45 minutes amount of barbiturate in blood gets 118 mkg/ml.

Blood extracorporeal regeneration (correction) procedure was conducted using the expedient equipment (UKBZH-1). The animal's blood was retrieved in portions of 10 ml, being then blended in equal volume proportions with ferreed sorbent suspension in physiological solution, which contained (mass. %): ferreed sorbent (core—nickel flake, coat inner layer—carbon, coat outer layer—dextran)—1.5; anticoagulant (heparin)—0.015; physiological solution as the balance; then the blood was sustained within 2-3 seconds and administered back into animal's organism.

About one liter of blood had been treated/processed during one session.

Indications before and after the correction session:

| Creatinine (m mole/l) | 1.45 | 1.10. |
| Urea (m mole/l) | 11.9 | 6.2. |
| Bilirubin (total) (m mole/l) | 25.0 | 14.4. |
| Barbiturates (mkg/ml) | 141.5 | 14.2. |

Furthermore, gastric lavage was made during the session, the animal was injected intravenously 500 ml of solution of electrolytes and 2% glucose.

After the session, the animal was in the state of moderate severity, brisk reflexes.

The indications of sorbate effectiveness are shown in the following examples below, as well as effectiveness of selective and functional properties of know ferreed sorbents, described, e.g. in the specifications of Russian Federation 2178313, and the results received during the researches with ferreed sorbent being proposed in this invention.

Example 2

5 ml of carbofos solution was injected into the test-tube with 100 ml of a non-pedigree dog blood. Carbofos concentration in the blood was 0.015 mkg/ml.

The received blend was divided in two parts and each part was added 20 ml of ferreed sorbent suspension, where in one part was added the known ferreed sorbent suspension in physiological solution (cores as iron particles, coat layers as silicon oxide) in the amount of 1.0 g, while in the second part was added the proposed ferreed sorbent with the same material composition but with flake cores, in the amount of OD g.

After mixing of the received compositions within 1.5 minutes the supernatant fluid was decanted, and the precipitate was withhold using a magnet.

Carbofos concentration in the supernatant fluid received from the first blend made 0.002 mkg/ml, and the supernatant fluid received from the second blend made 0.012 mkg/ml.

Example 3

Into two different test-tubes each containing 20 ml of blood serum of a dog with simulated nephratonia (urea concentration in the first test-tube was 26.4 m mole/l, and 30.2 m mole/l in the second), the following had been added: 200 mg of the known ferreed sorbent with the coating of SEPHADEX®-10 fermented with urease into the first test-tube; 30 mg of the ferreed sorbent being proposed with the cores in the form of titanium flakes with the coating analogous to the above specified, into the second test-tube.

After sustaining (while shaken) of the received compositions within 5 seconds and removal of the supernatant fluid in magnetic field, the urea content concentration in supernatant fluid in the first test-tube got—10.7 m mole/l, and got 12.1 m mole/l in the second one.

Example 4

In two different test-tubes each containing 20 ml of phosphoric acid sodium saline solution ($NaH_2PO_4$) in water the following had been added: 100 mg of the known ferreed sorbent with cation-modified (COON group polysaccharides) ion-exchange resin coating into the first test-tube, and 10 mg of the ferreed sorbent being proposed in the form of tantalum flakes with the coating analogous to the above specified—into the second test-tube.

After mixing (while shaken) of the received compositions and removal of the supernatant fluid in magnetic field, the concentration of phosphates in the supernatant fluid received from the first test-tube had reduced for 57% comparatively to the initial, and the concentration of phosphates in the supernatant fluid from the second test-tube; correspondingly, had reduced for almost half (for 44.8%) from the initial point of phosphates concentration.

Example 5

In two different test-tubes each containing 20 ml of sulphuric acid salines solution in water the following had been added: 100 mg of the known ferreed sorbent with anoinite-modified ($NH_3x"$ group) ion-exchange resin coating into the first test-tube, and 20 mg of the ferreed sorbent being proposed in the form of iron-nickel flakes with the coating analogous to the above specified—into the second test-tube.

After mixing (while shaken) of the received compositions and removal of the supernatant fluid in magnetic field, the concentration of sulphuric acid salines in the supernatant fluids received from both of the test-tubes had reduced virtually for the same, i.e. for 72% comparatively to the initial concentration in the first test-tube, and for 73.4% comparatively to the initial concentration—in the second test-tube.

Example 6

In two different test-tubes each containing 20 ml of blood of a patient with chronic renal-hepatic insufficiency disease the following had been added: 100 mg of the known ferreed sorbent with zirconium luminole saline-modified dextran coating into the first test-tube; and 30 mg of the ferreed sorbent being proposed in the form of iron-titanium flakes with the coating analogous to the above-specified—into the second test-tube.

After mixing (while shaken) of the received compositions and removal of the supernatant fluid in magnetic field, the concentration of phosphoric acid salines ($NaH_2PO_4$) in the supernatant fluid received from the first test-tube had got 0.07 mg/ml; and the concentration of phosphoric acid salines ($NaH_2PO_4$) in the supernatant fluid received from the second test-tube had got 0.021 mg/ml. The initial concentration of the saline was 0.61 mg/ml.

Example 7

In two different test-tubes each containing 10 ml of blood serum of a patient with chronic renal-hepatic insufficiency disease the following had been added: 50 mg of the known ferreed sorbent with iron-nickel cores and urease-modified SEPHADEX® coating into the first test-tube; and 10 mg of the ferreed sorbent being proposed with iron-nickel cores with coating analogous to the above-specified—into the second test-tube.

After sustaining within 10 seconds and the supernatant fluid decanting (sorption) the urea concentration in the supernatant fluid received from the first test-tube had reduced for 23% comparatively to the initial urea concentration in blood serum, and the urea concentration in the supernatant fluid received from the second test-tube had reduced for 35% comparatively to the initial urea concentration in the blood serum.

Example 8

In two different test-tubes each containing 20 ml of blood serum of a patient with sepsis the following had been added: 150 mg of the known ferreed sorbent with iron-nickel cores and oxaccillin-modified gelatin coating into the first test-tube; and 15 mg of the ferreed sorbent being proposed with iron-nickel-titanium-tantalum alloy flake cores with coating analogous to the above-specified—into the second test-tube.

After mixing while shaking of the test-tubes contents within 2 minutes, the supernatant fluid was decanted and the hard constituent was retained using a magnet field.

Inoculation was made both on the patient's blood agar-agar and the blood having been exposed to ferreed sorbent (the supernatant fluids) from the both test-tubes.

Growth of streptococcus and staphylococcus colonies was observed in the inoculation of the patients' blood; and no such growth was observed in the inoculation of the blood taken from the test-tubes.

Example 9

In two different test-tubes each containing 10 ml of lymph plasma of a patient with sepsis the following had been added: 100 mg of the known ferreed sorbent with iron-nickel cores and dextran coating into the first test-tube; and 15 mg of the ferreed sorbent being proposed with iron-nickel-titanium-tantalum alloy flake cores with coating analogous to the above-specified—into the second test-tube.

After mixing (while shaking) of the compositions received and removal of the supernatant fluid in magnetic field, inoculation was made both on the patient's lymph agar-agar and the lymph having been exposed to ferreed sorbent (the supernatant fluids) from the both test-tubes.

Growth of multiple staphylococcus colonies was observed in the inoculation of the lymph with no lymph-separation; virtually no such growth was observed in the inoculation of the supernatant fluids taken from the test-tubes.

Example 10

In two different test-tubes each containing 5 ml of blood-tinted cerebrospinal fluid (a patient with craniocerebral injury) the following had been added: 50 mg of the known ferreed sorbent with iron cores and silicon oxide coating into the first test-tube; and 15 mg of the ferreed sorbent being proposed with iron-tantalum alloy flake cores with coating analogous to the above-specified—into the second test-tube.

After sedimentation the cerebrospinal fluid in the test-tubes had got light yellow color.

Effectiveness of the developed preparation application is confirmed by the experiments when doing the research on sorption capacity of the ferreed sorbent for each above-described variation for its performance, and at the same time the results are commensurable to the results of using analogous variations of the known ferreed sorbent were achieved at using significantly lower amounts of the ferreed sorbent being proposed.

What is claimed is:

1. A method of extraction of a sorbent, comprising:
   volatizing or fusing a powder of at least one of iron, nickel, titanium, or tantalum in a low-temperature plasma at a first temperature of $10^4 \times (0.5\text{-}5)$ K,
   quenching and condensing at least one of received vaporous or fused particles of one of metal products or metal alloy products in a gas flow,
   precipitating a precipitate product in a form of crystals or metal alloy microbars,
   transferring the precipitate product into a dispersion medium containing stabilizer,
   mixing the dispersion for (5-15) hours at a second temperature of (50-90)° C. and at a residual pressure of 1-5 mmHg until an end of a gas liberation,
   flattening the crystals or the microbars into flakes of a predetermined thickness,
   washing the flakes in distilled water more than once,
   removing weak parts of the flakes by ultrasound at a (200-300) $W/cm^2$ intensity,
   drying the flakes in a hot air sterilizer at a third temperature of (80-110)° C.,
   fractionating the flakes in an inert gas flow with a velocity of (0.02-1.00) m/s at an exposure of a magnetic field with an intensity of $(10\text{-}10^3)$ A/m and by centrifugation,
   educing sorbent cores of a specified dimension, on each of which a coat is formed layer-by-layer, and
   packing and sterilizing the sorbent cores as an end product in a light-proof hermetically sealed container.

2. The method of claim 1, further comprising coating the flakes.

3. The method of claim 1, wherein a first closest layer to a core layer of the coat is formed by thermal treatment of the fractionated flakes at (1000-1500)° C. in the inert gas flow containing microparticles of one of carbon, silicon dioxide, aluminium oxide, or zirconium oxide.

4. The method of claim 1, wherein a first layer of the coat is formed though mixing using an ultrasound exposure to the fractionated flakes suspension within (1-10) minutes in a heated aqueous solution of one of dextran, gelatin, albumin, or amylum up to (30-80)° C. with subsequent quenching of the suspension down to (4-10)° C., and a received precipitate is filled up with a formalin and sustained therein within (10-40) minutes while simultaneously mixing, then is thoroughly dried out at (25-50)° C., and is grinded, and the received end product is filtered in a magnetic field.

5. The method of claim 1, wherein a first layer of the coat is formed by adding an ion-exchange resin into the suspension of fractionated flakes in distilled water at (40-60)° C., with subsequent cooling of the above suspension down to the temperature of (15-30)° C. and adding nitrous acid ($HNO_2$) diluted in water, sustaining within (10-15) minutes, cooling down to (4-10)° C. and extracting of a precipitate which then is washed in the physiological solution, and buffered in an aqueous solution of a blend of $NH_4OH$ foundation and $NH_4Cl$ saline.

6. The method of claim 1, wherein a second layer of the coat is formed through mixing by ultrasound exposure within (1-10) minutes to a ferromagnetics suspension covered with one of carbon, silicon dioxide, aluminium oxide, or zirconium oxide coating in a (30-80)° C. aqueous solution of one of dextran, gelatin, albumin, or amylum with subsequent cooling of the suspension to (4-10)° C., and the received precipitate is filled up with formalin and sustained therein within (10-40) minutes while simultaneously being mixed, and then is thoroughly dried out at (25-50)° C., and grinded and the received end product is filtered in a magnetic field.

7. The method of claim 1, wherein a second layer of the coat is formed by adding an ion-exchange resin into suspension in distilled water of ferromagnetics covered with one of a carbon, silicon dioxide, aluminium oxide, or zirconium oxide coating heated to (40-60)° C., with subsequent cooling of the suspension down to (15-30)° C., and adding while being mixed albumin with subsequent adding of nitrous acid ($HNO_2$) diluted in water, sustaining within (10-15) minutes, cooling down to (4-10)° C. and extracting a precipitate which then is activated by sustaining within (1.5-2) hours in a modifier solution, washed in a physiological solution, and buffered to reach a pH 4.0-0.5 in an aqueous solution of a blend of $NH_4OH$ foundation and $NH_4Cl$ saline.

8. The method of claim 7, wherein one of a sodium periodate (NaIO4) or a glutaric dialdehyde in (3-10) % aqueous solution of $Na_2SO_4$ is used as a modifier.

9. The method of claim 7, wherein while forming an outer layer of the coat the outer layer is conjugated with antibodies by adding into the aqueous suspension of ferreed sorbent with one of the single layer coating and the double layer coating, the outer layer is made of one of SEPHADEX® or albumin and modified with one of glutaric dialdehyde or sodium periodate of serum containing antibodies specific to an antigen being sorbed in a buffered fluid with a pH of 6.5-10, further sustaining of the composition while being mixed within (1-3) hours at (15-25)° C., subsequently adding sodium borhydrate into the composition, cooling to (4-10)° C., and repeated sustaining while mixing within (1-3) hours, extraction of the precipitate and its buffering and drying out.

10. The method of claim 7, wherein while forming an outer layer of the coat the outer layer is modified by a pharmaceutical preparation by heating the suspension of the ferreed sorbent with the one of the single layer coating or the double layer coating, the outer layer made of one of dextran or gelatin heated to (35-70)° C. in a physiological solution and adding a pharmaceutical preparation powder and sustaining while thoroughly being mixed at (0.5-2.5) hours, then cooling the compound to (4-10)° C., decanting of a supernatant fluid in a magnetic field, and washing the precipitate in running distilled water and then drying out.

11. The method of claim 7, wherein while forming an outer layer of the coat the outer layer is modified through preliminary dilution of urease crystals in a polyether, mixture of the composition with suspension in distilled water of the ferreed sorbent with the coating made of SEPHADEX®, then sustaining while being mixed at (25-40)° C. within (2-5) hours and cooling to (4-10)° C., then adding a formaldehyde and repeated sustaining within (1-3) hours, and removal of a supernatant fluid under exposure of a magnetic field and then precipitate drying out.

12. The method of claim 7, wherein while forming an outer layer of the coat the outer layer is modified through heating of an aqueous suspension of the ferreed sorbent with the coating made of dextran, up to (40-70)° C., with subsequent mixing with one of zirconium saline powder and phthalhydrazide saline, and a (50-120) $W/cm^2$ intensity ultrasound exposure within (1-10) minutes, cooling of the received blend to (4-10)° C., adding the formaldehyde, sustaining while being mixed within (1-3) hours, and removal of supernatant fluid under the exposure of a magnetic field and then drying out the precipitate.

13. The method of claim 1, further comprising coating with a one-layer coat including carbon, aluminium oxides, silicon oxide, zirconium dioxide, dextran, gelatin, albumin, polysaccharide, amylum, ion-exchange resins, cations or anions.

14. The method of claim 13, further comprising coating with an outer layer including dextran, gelatin, albumin, polysaccharide, amylum, ion-exchange resins, cations or anions.

15. The method of claim 14, wherein the outer layer of the coat is made by one of conjugation with antibodies, modification with a pharmaceutical preparation, including one of antibiotics, phthalhydrazide salines, 5-amino-2,3-dihydro-1, 4-dione salines, or fermented.

* * * * *